United States Patent
An et al.

(10) Patent No.: US 12,235,253 B2
(45) Date of Patent: Feb. 25, 2025

(54) SYSTEMS AND METHODS FOR GENERATING WATER TREATMENT PLANS

(71) Applicants: Jun Su An, Houston, TX (US); Thomas Swanson, Houston, TX (US); Paul T. Schuber, Houston, TX (US); Andrew Mordh, Houston, TX (US)

(72) Inventors: Jun Su An, Houston, TX (US); Thomas Swanson, Houston, TX (US); Paul T. Schuber, Houston, TX (US); Andrew Mordh, Houston, TX (US)

(73) Assignee: SOLUGEN, INC., Houston, TX (US)

(*) Notice: Subject to any disclaimer, the term of this patent is extended or adjusted under 35 U.S.C. 154(b) by 324 days.

(21) Appl. No.: 17/788,279

(22) PCT Filed: Feb. 5, 2021

(86) PCT No.: PCT/US2021/016771
§ 371 (c)(1),
(2) Date: Jun. 22, 2022

(87) PCT Pub. No.: WO2021/158889
PCT Pub. Date: Aug. 12, 2021

(65) Prior Publication Data
US 2023/0024753 A1   Jan. 26, 2023

Related U.S. Application Data

(60) Provisional application No. 62/971,106, filed on Feb. 6, 2020.

(51) Int. Cl.
*G01N 33/18* (2006.01)
*C02F 1/00* (2023.01)
(Continued)

(52) U.S. Cl.
CPC .............. *G01N 33/18* (2013.01); *C02F 1/008* (2013.01); *C02F 3/006* (2013.01); *G06N 3/08* (2013.01); *C02F 2103/10* (2013.01)

(58) Field of Classification Search
CPC . B01D 2201/54; B01D 2201/56; C02F 1/008; C02F 2103/10; C02F 3/006; G01N 33/18; G06N 3/08
See application file for complete search history.

(56) References Cited

U.S. PATENT DOCUMENTS 6,408,227 B1 * 6/2002 Singhvi ................ G05B 13/027
                                                                    700/32
6,560,543 B2   5/2003 Wolfe et al.
(Continued)

FOREIGN PATENT DOCUMENTS

WO   2017/188858 A1   11/2017

OTHER PUBLICATIONS

International Patent Application No. PCT/US2021/016771 Search Report and Written Opinion dated Apr. 23, 2021 (18 pages).

*Primary Examiner* — Michael J Dalbo
(74) *Attorney, Agent, or Firm* — CONLEY ROSE, P.C.

(57) ABSTRACT

A method for determining a water treatment plan for produced water includes receiving sample water analysis for the produced water, and receiving one or more key performance indicators (KPIs) that each indicate a selected treatment result for the produced water. In addition, the method includes providing the sample water analysis and the KPIs to a machine learning model and determining a water treatment plan for the produced water using the machine learning model, wherein the water treatment plan comprises one or more additives for the produced water that are to provide the produced water with the KPIs.

18 Claims, 4 Drawing Sheets

(51) Int. Cl.
*C02F 3/00* (2023.01)
*C02F 103/10* (2006.01)
*G06N 3/08* (2023.01)

(56) References Cited

U.S. PATENT DOCUMENTS

| | | |
|---|---|---|
| 6,845,336 B2 | 1/2005 | Kodukula et al. |
| 9,605,529 B1 | 3/2017 | Venter et al. |
| 9,791,427 B2 | 10/2017 | Mori et al. |
| 2003/0234218 A1* | 12/2003 | Yang .................... G05B 13/027 |
| | | 210/614 |
| 2010/0224365 A1* | 9/2010 | Abad ...................... E21B 43/26 |
| | | 166/275 |
| 2015/0196002 A1 | 7/2015 | Friesth |
| 2015/0368592 A1* | 12/2015 | Cabanas .................. C11D 7/06 |
| | | 134/22.13 |
| 2016/0042272 A1 | 2/2016 | Mohaghegh |
| 2016/0063402 A1 | 3/2016 | Webb et al. |
| 2017/0096881 A1 | 4/2017 | Dusterhoft et al. |
| 2019/0323330 A1* | 10/2019 | Zimmerman Frisby .. C02F 1/76 |
| 2020/0231466 A1* | 7/2020 | Lu .......................... G01N 33/18 |
| 2021/0263490 A1* | 8/2021 | Ueno ....................... C02F 1/00 |
| 2022/0004886 A1* | 1/2022 | Exner ................... G06N 5/022 |
| 2023/0199117 A1* | 6/2023 | Koul .................. H04M 3/5183 |
| | | 379/201.01 |

* cited by examiner

SYSTEMS AND METHODS FOR GENERATING WATER TREATMENT PLANS

CROSS-REFERENCE TO RELATED APPLICATIONS

This application is a National Phase Entry into the U.S. under 35 U.S.C. § 371 of and claims priority to PCT Application No. PCT/US2021/016771 filed Feb. 5, 2021, and entitled "Systems and Methods For Generating Water Treatment Plans," which claims the benefit of U.S. Provisional Application Ser. No. 62/971,106 filed Feb. 6, 2020, and entitled "System and Method For Water Treatment Recommendations," the contents of which are incorporated herein by reference in their entirety for all purposes.

STATEMENT REGARDING FEDERALLY SPONSORED RESEARCH OR DEVELOPMENT

Not applicable.

BACKGROUND

Operations for completing, stimulating, treating, etc. a subterranean wellbore (e.g., such as a wellbore drilled to access subterranean hydrocarbon deposits) may involve the injection of water into the wellbore. Various factors may influence the amount of water that is injected to a wellbore during operations, such as, for instance, the amount of proppant and/or water consumed per lateral foot along the wellbore, and the total length of the wellbore or portion thereof (e.g., such as a length of a lateral section of the wellbore). Accordingly, in some situations the total volume of water injected into a particular wellbore may be substantial during operations.

BRIEF SUMMARY

Some embodiments disclosed herein are directed to a method for determining a water treatment plan for produced water. In some embodiments, the method includes receiving sample water analysis for the produced water, and receiving one or more key performance indicators (KPIs) that each indicate a selected treatment result for the produced water. In addition, the method includes providing the sample water analysis and the KPIs to a machine learning model. Further, the method includes determining a water treatment plan for the produced water using the machine learning model, wherein the water treatment plan comprises one or more additives for the produced water that are to provide the produced water with the KPIs.

Some embodiments disclosed herein are directed to a system for determining a water treatment plan for produced water. In some embodiments, the system includes an input device, an output device, and a water treatment plan generator coupled to the input device and the output device. The water treatment plan generator is to receive water sample analysis for the produced water via the input device, and receive one or more key performance indicators (KPIs) for the produced water via the input device, wherein each of the KPIs indicate a selected treatment result for the produced water. In addition, the water treatment plan generator is to provide the sample water analysis and the KPIs to a machine learning model, determine a water treatment plan for the produced water using the machine learning model, wherein the water treatment plan comprises one or more additives for the produced water that are to provide the produced water with the KPIs, and communicate the water treatment plan to the output device.

Some embodiments disclosed herein are directed to a non-transitory, machine-readable medium comprising instructions, that when executed by a processor, cause the processor to: receive sample water analysis for produced water that originated from a subterranean formation; receive one or more key performance indicators (KPIs) that each indicate a selected treatment result for the produced water; provide the sample water analysis and the KPIs to a machine learning model; and determine a water treatment plan for the produced water using the machine learning model, wherein the water treatment plan comprises one or more additives for the produced water that are to provide the produced water with the KPIs.

Embodiments described herein comprise a combination of features and characteristics intended to address various shortcomings associated with certain prior devices, systems, and methods. The foregoing has outlined rather broadly the features and technical characteristics of the disclosed embodiments in order that the detailed description that follows may be better understood. The various characteristics and features described above, as well as others, will be readily apparent to those skilled in the art upon reading the following detailed description, and by referring to the accompanying drawings. It should be appreciated that the conception and the specific embodiments disclosed may be readily utilized as a basis for modifying or designing other structures for carrying out the same purposes as the disclosed embodiments. It should also be realized that such equivalent constructions do not depart from the spirit and scope of the principles disclosed herein.

BRIEF DESCRIPTION OF THE DRAWINGS

For a detailed description of various exemplary embodiments, reference will now be made to the accompanying drawings in which.

DETAILED DESCRIPTION

The following discussion is directed to various exemplary embodiments. However, one of ordinary skill in the art will understand that the examples disclosed herein have broad application, and that the discussion of any embodiment is meant only to be exemplary of that embodiment, and not intended to suggest that the scope of the disclosure, including the claims, is limited to that embodiment.

The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection.

Thus, if a first device couples to a second device, that connection may be through a direct connection of the two devices, or through an indirect connection that is established via other devices, components, nodes, and connections. In addition, as used herein, the terms "axial" and "axially" generally mean along or parallel to a given axis (e.g., central axis of a body or a port), while the terms "radial" and "radially" generally mean perpendicular to the given axis. For instance, an axial distance refers to a distance measured along or parallel to the axis, and a radial distance means a distance measured perpendicular to the axis. Further, when used herein (including in the claims), the words "about," "generally," "substantially," "approximately," and the like mean within a range of plus or minus 10%.

As previously described, a well operator may inject substantial volumes of water into a subterranean wellbore during operations (e.g., stimulation operations, completion operations). For instance, referring now to FIG. 1, a subterranean wellbore environment 2 is shown. The wellbore environment 2 includes a borehole 4 extending into a subterranean formation 6 from the surface 7. One or more tubulars 5 (e.g., casing pipes, production tubing, completion string, etc.) may be inserted within the borehole 4. Some of these tubulars 5 may be secured within borehole 4 via cement 8 (e.g., such as in the case of casing pipes). Surface equipment 3 may be disposed at surface 7 and coupled to borehole 4. Generally speaking, surface equipment 3 may include any suitable surface components such as a wellhead, drilling rig, etc. Throughout the operational life of borehole 4 (e.g., drilling, completion, stimulation, production, etc.), it may be desirable to conduct operations whereby fluids, including water, are pumped or flowed into the borehole 4 and/or formation 6. For instance, hydraulic fracturing (or "fracking") operations may be conducted that involve the pumping of water and proppant into the borehole 4 to generate fractures within the formation 6 that then serve as flow paths for formation fluids (e.g., liquid hydrocarbons, hydrocarbon gases, water, etc.) into borehole 4, tubulars 5, and subsequently to the surface 7 during production operations.

Figure 1:
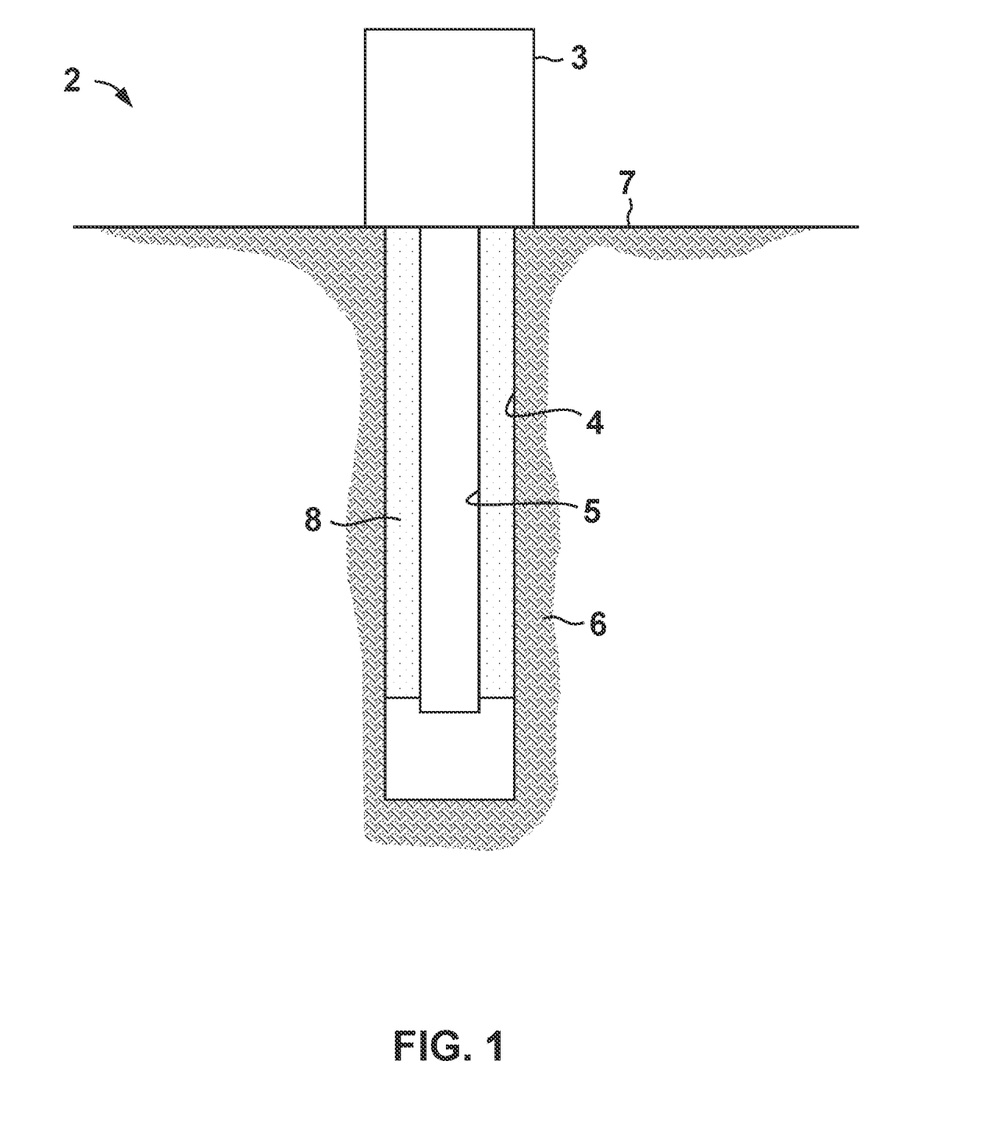
FIG. 1 is a side view of a wellbore environment.

The source of the water utilized for fracking or other types of wellbore operations involving water injection may heavily impact the overall time, costs, efficacy of the wellbore operations. In particular, fresh water that is sourced from a location independent of borehole 4 may provide suitable characteristics for improving the efficacy of the water injection operations and may avoid detrimental effects within the wellbore (described in more detail below). However, the availability of fresh water may be limited, and the costs for sourcing (e.g., including transportation and disposal costs) the fresh water may be prohibitively high. Thus, well operators may attempt to use water produced from the formation 6 via the borehole 4 or another borehole communicating with the formation 6 for water injection operations so as to avoid the additional costs associated with fresh water. The water produced from a subterranean wellbore (e.g., wellbore 4) may be referred to herein as "produced water." In some embodiments, produced water may comprise water formation water, flowback water, blackwater, brines of greater than 25000 mg/L total dissolved solids (TDS), etc.

However, reusing untreated produced water can result in detrimental effects in the wellbore 4 and formation 6. For example, in the absence of a biocide, produced water may demonstrate an increase in sulfate reducing bacteria (SRBs) and/or acid producing bacteria (APB). SRB can cause well to sour as a result of hydrogen sulfide ($H_2S$) production, which can substantially impact the normal operation of wellbore 4. APB can increase corrosion in the wellbore 4, which can create issues with well integrity, construction, zonal isolation/communication, and produced fluid contact with water tables or the surface 7.

In addition, the absence of a scale inhibitor in the injected, produced water may allow scale to buildup, which increases the pressure drop in the wellbore 4 and can result in increased utility cost for artificial lift, pump jacks, and choked production. Further, without adequate oil/water separation (e.g., via non-emulsifiers), produced water may not meet requirements for more cost-effective treatment routes (e.g., pit treatment). Also, inadequate oil/water separation results in lost product and revenue, and as hydrocarbon content of produced water increases, emulsion efficacy can be negatively affected.

Still further, iron-control can affect may multiple aspects of a produced water treatment process. For example, in the absence of an iron-control agent, polymer hydration of polymer additives (e.g., viscosifiers) can be undesirably inhibited, resulting in lower or diminished viscosity yield. Also, in the absence of an iron-control agent, free iron in the water undesirably accelerates the decomposition of breakers (e.g., oxidizers), which can result in increased in oxidizer breaker usage. Also, in the absence of an iron-control agent, free iron in the water leads to loss in efficacy for certain scale inhibitors (e.g., phosphonate scale inhibitors), thereby resulting in an increase in minimum inhibitor concentration (MIC) to prevent the formation of calcite scale.

Accordingly, well operators may treat produced water with various additives and agents to avoid these detrimental effects. However, the particular combination (including relative amounts) of these additives is often dictated by the very particular attributes of the produced water, the subterranean formation, etc., as well as the performance requirements of the wellbore (e.g., which may be dictated by the operator). So, for each wellbore, produced water source, and/or wellbore operation, the optimum combination of treatment additives (and/or their relative amounts) may be different.

In some circumstances, well operators may utilize an iterative method for determining the optimum treatment plan for produced water. Specifically, such a process may involve extensive "bottle tests," in which operators iteratively dose samples of produced water with additives and assign a qualitative, relative ranking that eventually determines the additive selection and dosage for the produced water in general. However, such an interactive process is time consuming and may not ultimately result in an optimized treatment plan.

Accordingly, embodiments disclosed herein include systems and methods for determining a water treatment plan for produced water that may offer a higher level of efficiency. In some embodiments, the systems may comprise a water treatment plan generator that provides various inputs (e.g., parameters of the produced water, wellbore, subterranean formation) to a machine learning model and that outputs a water treatment plan including a list of additives and their relative amounts. Thus, through use of the embodiments disclosed herein, a well operator may more quickly and efficiently arrive at an optimized water treatment plan for produced water.

Figure 2:
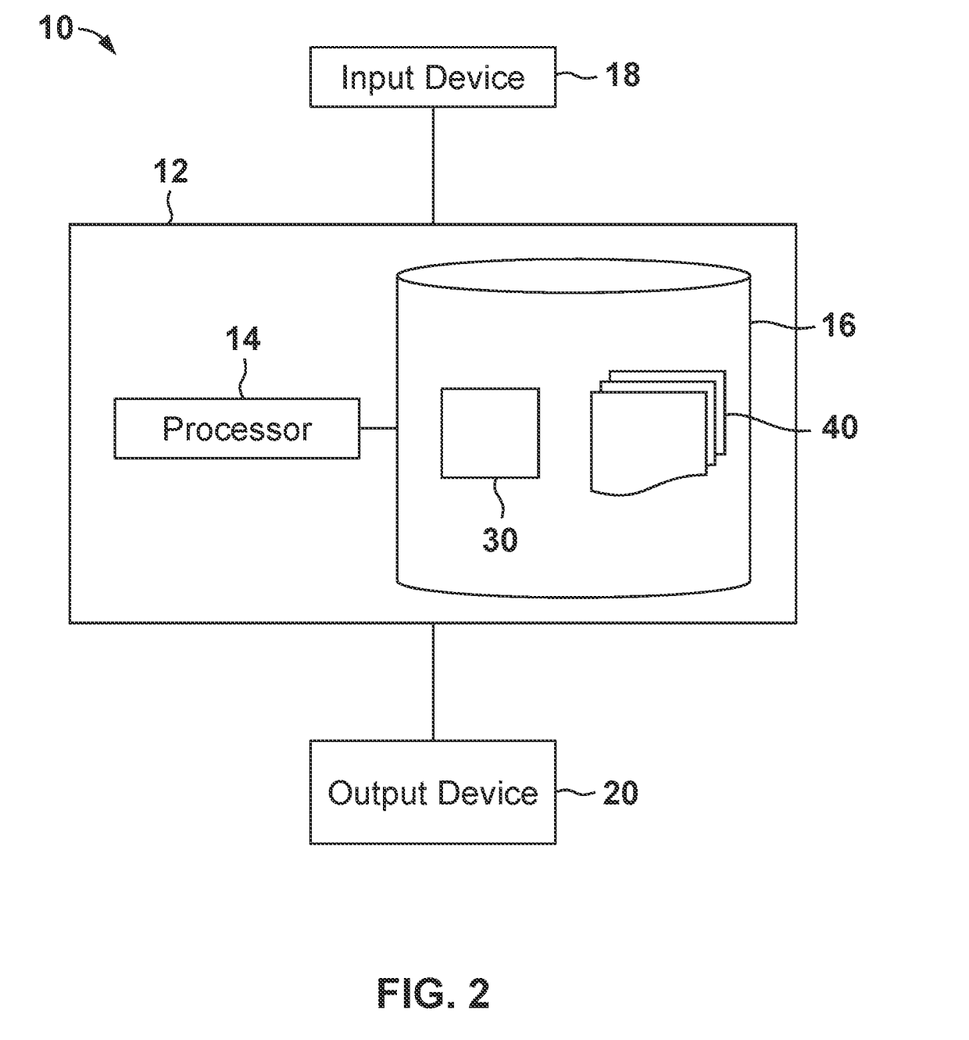
FIG. 2 is a schematic diagram of a system for determining a water treatment plan according to some embodiments.

Referring now to FIG. 2, a system 10 for generating a water treatment plan for produced water according to some embodiments is shown. System 10 generally includes a water treatment plan generator 12 that may comprise one or more computing devices (e.g., computers, servers, etc.) further comprising a processor 14 and a memory 16.

The processor 14 may comprise any suitable processing device, such as a microcontroller, central processing unit (CPU), graphics processing unit (GPU), timing controller (TCON), a scaler unit. The processor 14 executes machine-readable instructions (e.g. machine-readable instructions 30) stored on memory 16, thereby causing the processor 14 (and, more generally, water treatment plan generator 12) to perform some or all of the actions attributed herein to the processor 14 (and, more generally, to water treatment plan generator 12). More specifically, processor 14 fetches, decodes, and executes instructions (e.g., machine-readable instructions 30). In addition, processor 14 may also perform other actions, such as, making determinations, detecting conditions or values, etc., and communicating signals. If processor 14 assists another component in performing a function, then processor 14 may be said to cause the component to perform the function.

The memory 16 may comprise volatile storage (e.g., random access memory (RAM), non-volatile storage (e.g., flash storage, read-only memory (ROM)), or combinations of both volatile and non-volatile storage. Data read or written by the processor 14 when executing machine-readable instructions can also be stored on memory 16. Memory 16 may comprise a "non-transitory machine readable medium."

The processor 14 may comprise one processing device or a plurality of processing devices that are distributed throughout water treatment plan generator 12. Likewise, the memory 16 may comprise one memory device or a plurality of memory devices that are distributed throughout water treatment plan generator 12.

In addition to machine-readable instructions 30, memory 16 may also comprise one or more databases 40, which may store information for facilitating the functionality of water treatment plan generator 12 as described herein. The one or more databases 40 may comprise a single database 40 or a plurality of databases 40 that are accessible by processor 14 during operations. For convenience, the one or more databases 40 will be more simply referred to herein as "databases" 40. In some embodiments, the databases 40 may comprise independent data tables. In some embodiments, databases 40 may comprise multiple, interrelated data tables. For instance, in certain embodiments, databases 40 (or some of the databases 40) may be relational databases, and as such, primary and foreign key relationships may be enforced to ensure data integrity within each database 40 and/or between the databases 40, as described herein.

In some embodiments, databases 40 may comprise information that is used to train and/or refine a machine learning model (e.g., water treatment model described in more detail below) for determining water treatment plans for produced water. In particular, databases 40 may comprise historical water analysis information, which may comprise analysis information of produced water sources (or samples thereof). In some embodiments, the historical water analysis information may comprise a collection of parameters and characteristics of the plurality of produced water sources. In some embodiments, the samples of produced water used to generate the historical water analysis information may comprise produced water samples from a particular subterranean wellbore, and/or reservoir. In some embodiments, the samples of produced water used to generate the historical water analysis information may comprise samples of produced water from a plurality of wellbores, reservoirs, depths, regions, countries, etc. The historical water analysis information may comprise information related to samples of produced water that have not been treated with any additives as described herein as well as information related to samples of produced water that have been treated with one or more additives as described herein.

The parameters and characteristics of the produced water comprising the historical water analysis information stored in the databases 40 may be derived from various tests, observations, and analysis performed on the samples of produced water. For example, in some embodiments, the historical water analysis information may comprise water source data, which may include source details about a particular produced water sample. This may include, for example, global positioning system (GPS) coordinates, identifying information for a well site (e.g., formation depth, geophysical markers and/or logs, formation characteristics), a geographical region, a regional biome type, a time, a date, or any other suitable information regarding where and when the produced water sample was collected. In some embodiments, the water source data may include details regarding the water analysis, such as a location at which the analysis was performed, the identity of the person performing the analysis, the type of analysis performed, the equipment used to perform the analysis, or any other suitable information regarding the produced water sample analysis.

In addition, the historical water analysis information stored in databases 40 may comprise the results of each sample analysis. For example, in some embodiments, a principal component analysis (PCA) may be performed on the produced water samples that identifies and quantifies each species (e.g., cations, anions, dissolved solids, hydrocarbon content) present in the corresponding produced water sample. As such, the historical water analysis information may include a list of the components detected within the produced water sample, as well as the concentrations of each of these components. In some embodiments, the historical water analysis information may include other measurements performed on the produced water sample(s), such as measurements of TDS, turbidity, pH, alkalinity, dissolved organic content (DOC), and so forth.

Referring still to FIG. 2, in some embodiments, databases 40 may comprise historical water treatment information, which may comprise information related to the treatment and treatment results of the produced water samples utilized to generate the historical water analysis information. Accordingly, in some embodiments, the water historical treatment information may be related to the historical water analysis information within the databases 40 as generally described above (e.g., via a primary key values or other unique identifiers). In some embodiments, the historical water treatment information may include identifying data for a post-treatment produced water sample analysis also stored in the databases 40 as historical water analysis information as described above.

In some embodiments, historical water treatment information stored in databases 40 may comprise information related to a treatment (or treatments) performed on the one or more produced water samples. For instance, the historical water treatment information may include location data for where the treatment was performed, a time and date of the treatment, the worker performing the treatment, ambient conditions during the treatment, and so forth.

In some embodiments, the historical water treatment information may also include an indication of whether the treatment is indicative of a particular type of test on the produced water sample(s), such as a bottle test or a field test. As previously described, a bottle test may comprise treatments and analysis of relatively small samples of produced water. On the other hand, field test treatments may comprise treatments and analysis of larger volumes of water within particular field environment, such as, for instance within a wellbore (e.g., wellbore 4 in FIG. 1). In some embodiments, a field test may also include treatment of produced water at a water treatment facility, treatment of produced water within an in-line pipeline, treatment of produced water during truck transport, treatment of produced water a large-scale water pit. Water treatment information that is indicative of a field test may comprise details regarding the field test, such as an identity of a well site and initial operating conditions of the well (e.g., injection rate, injection pressure) when the test was performed.

In some embodiments, the historical water treatment information stored in databases 40 may comprise details about the treatment additives and their relative amounts for the produced water samples. A water treatment plan may include the addition of any suitable number of treatment additives to a produced water sample. For example, treatment additives may include, but are not limited to: oxidizers (e.g., breakers), biocides, reducing agents (e.g., reducers), scale inhibitors, corrosion inhibitors, chelating agents (e.g., iron control agents), coagulants, viscosifiers, rheology modifiers, dispersants, flocculants, floatation aids, surfactants, emulsifiers, demulsifiers, foamers, and defoamers. A chelating agent or chelant that may be used as a treatment additive may include an aldonic, uronic, or aldaric acid, typically in the presence of an alkali metal (Group I) or alkali earth metal (Group II) counter-cation. In some embodiments, the chelant may be a biochelant (or bio-based chelant) that is produced using a biological catalyst (e.g., an enzyme). For such embodiments, the cation counterpart may be sodium, potassium, calcium, or ammonium. In some embodiments, the chelant is a biochelant that includes a complex glucose or gluconic acid oxidation product buffered to a pH of 2.6-5.6 with sodium hydroxide that consists substantially of a mixture of gluconic acid and glucaric acid with minor component species comprising n-keto-acids and $C_2$-$C_6$ diacids. In some embodiments, the chelant is a biochelant that includes a complex glucose or gluconic acid oxidation product with a pH of 1-3. More particularly, the chelant comprises a mixture of gluconic acid and glucaric acid with minor component species comprising n-keto-acids and $C_2$-$C_6$ diacids. In some embodiments, the chelant comprises sugar oxidation products comprising of disaccharides, oxidized disaccharides, uronic acid, and aldaric acid. In some embodiments, the chelant comprises gluconic acid, glucaric acid, glucuronic acid, n-keto-acids and C2-C6 diacids.

In some embodiments, the historical water treatment information may include other details, such as a rate at which one or more of the treatment additives are introduced during treatment. In addition, in some embodiments, the historical water treatment information may comprise an order of addition and/or a timing of addition of one or more (or all) of the treatment additives during the treatment.

In some embodiments, the historical water treatment information may include treatment results for the produced water samples in the form of key performance indicators (KPIs or KPI). It may be appreciated that the KPIs of interest may be different for different water sources, treatments, and/or applications. For example, in some embodiments a KPI for a particular produced water sample may comprise an iron content, such as for instance, a value indicative of the reduction in iron content after treatment. In some embodiments, a KPI for a particular produced water sample may comprise a value indicating the TDS, such as for instance, a value indicative of a reduction in TDS after treatment. In some embodiments, a KPI for a produced water sample may comprise a value indicating the turbidity, such as for instance, a value indicative of the reduction in turbidity or an improvement in clarity after treatment. In some embodiments, for treatments that are field tests as described above, a KPI may comprise a value indicative of the increase in well injection rate after treatment, and/or a value indicative of the decrease in injection pressure after treatment. In some embodiments, a KPI for a particular produced water sample may be cost-related, such as for instance, a value indicative of the cost of the treatment per unit volume or a change in total operational costs per unit volume of product as a result of the treatment.

Generally speaking, during operations the water treatment plan generator 12 uses a machine learning model (referred to herein as a water treatment model) to identify correlations between the historical water analysis information and the historical water treatment information stored in databases 40 for purposes of determining a water treatment plan for new samples of produced water to achieve desired treatment results, which may be represented by selected KPIs. Accordingly, it is desirable for the historical water analysis information and historical water treatment information to include as many details as possible. For example, even if a treatment was performed on a produced water sample specifically to decrease the injection pressure within a wellbore, it is desirable for the water treatment information to include other KPIs (e.g., injection rate, iron counts), such that the water treatment model used by the water treatment plan generator 12 may identify relationships and correlations that may not be determinable when only certain KPIs are stored and considered.

Referring still to FIG. 2, water treatment plan generator 12 is coupled to an input device 18 and an output device 20. The input device 18 may comprise one or a collection of devices that are configured to receive inputs from a user and/or another computing device. For instance, in some embodiments, input device 18 may comprise a computer mouse, keyboard, touchpad, and/or touch-sensitive display (e.g., such as a display of output device 20 as described below). During operations, a user may provide inputs in the form of water analysis, desired water treatment results, etc. to the water treatment plan generator 12 via the input device 18.

Output device 20 may comprise one or a collection of devices for outputting information (e.g., to a user). For instance, in some embodiments, the output device 20 may comprise an electronic display (e.g., computer monitor, television screen, smartphone display), a printer, and/or a speaker. During operations, a user may receive a water treatment plan from the water treatment plan generator 12 via the output device 20.

The input device 18 and/or output device 20 may be directly coupled to the water treatment plan generator 12. In some embodiments, one or both of the input device 18 and output device 20 may be positioned within (or coupled to) another device (e.g., computer, smartphone) that is coupled to water treatment plan generator 12 via a wired connection (e.g., cable, wire, fiberoptic) and/or a wireless connection (e.g., WIFI, BLUETOOTH®, near-field communication, infrared, radio frequency). In some embodiments one or both of the input device 18 and the output device 20 may be coupled to the water treatment plan generator 12 via a network (e.g., the Internet, a local network).

Referring still to FIG. 2, during operations water treatment plan generator 12 may determine a water treatment plan based on a water analysis for a sample of produced water and one or more selected treatment results. In particular, a well operator may wish to inject produced water into a wellbore. Accordingly, analysis may be performed on the produced water (or a sample or samples thereof) to produce the water analysis. The water analysis of the produced water may comprise the same types of information described above for the historical water analysis information stored in databases 40. In addition, one or more desired treatment results for the produced water may be determined and provided to the water treatment plan generator 12. In some embodiments, the one or more selected treatment results may comprise KPIs that are selected based on the water analysis of the produced water, the conditions or parameters of the wellbore or subterranean formation to receive the water injection, etc. For instance, if the water analysis indicates that the produced water has a higher iron content than is appropriate for injection into the wellbore, then the one or more selected treatment results may comprise a KPI related to the desired reduction in the iron content for the produced water.

The water analysis and selected treatment results (e.g., KPIs) may be provided to the water treatment plan generator 12 via input device 18 as generally described above. Thereafter, the water treatment generator 12 may determine (e.g., via processor 14 executing machine-readable instructions 30 as generally described above) a water treatment plan for the produced water. The treatment plan may include a list of additives to be provided to the produced water, as well as the relative amounts of additives, the order of addition of the additives, and/or the timing and/or manner of addition of the additives.

In some embodiments, the water treatment generator 12 may employ machine learning techniques to determine the water treatment plan. More particularly, the water treatment generator 12 may employ a water treatment model that receives the water analysis and the selected treatment results (e.g., KPIs) as inputs and that outputs a water treatment plan. The water treatment model may comprise one or more relationships between the historical water analysis information and the historical water treatment information that may then be applied to the water analysis and selected treatment results (e.g., KPIs) of the produced water in question so as to provide a water treatment plan that is to provide the desired treatment results (e.g., KPIs) for the produced water.

The water treatment model may utilize any suitable machine learning technique(s). In some embodiments, the water treatment model may comprise an artificial neural network (ANN), such as a deep neural network, convolutional neural network, or recurrent neural network. For example, the ANN may include one or more sets of interconnected nodes including weights to direct signal propagation between the nodes. In some embodiments, the water treatment model may comprise a Bayesian network, a decision tree, logistical regression, normalized logistical regression, k-means clustering, or any other supervised or unsupervised machine learning models.

The water treatment model may be trained using the historical water analysis information and historical water treatment information stored in the databases 40. For instance, for historical water analysis information and historical water treatment information in databases 40 may comprise labeled data that is provided to the water treatment model to derive the one or more parameters, coefficients, etc. for generating the water treatment plans during operations. For instance, when the water treatment model comprises an ANN as previously described, the ANN may utilize the labeled data (e.g., the historical water analysis information and historical water treatment information stored in databases 40) to adjust the weights of the nodes until the ANN provides the expected outputs (e.g., water treatment plans) that correlate to the historical water analysis information and historical treatment information stored in the databases 40. Thereafter, when the ANN is provided with the water analysis and selected treatment results (e.g., KPIs) for a new source of produced water under consideration, the trained ANN of the water treatment model may then apply the derived parameters, coefficients, etc. to output a water treatment plan as described above.

In some embodiments, the water analysis, selected water treatment results, and/or post-treatment water analysis of the produced water (e.g., treatment according to a water treatment plan determined by the water treatment plan generator 12) may be provided to the databases 40 as additional historical water analysis information and historical water treatment information as described above. The additional information in databases 40 may then be used to refine the parameters, coefficients, etc. of the water treatment model in the manner described above. For instance, the weights of ANN may be further refined (e.g., using a suitable evolutionary algorithm, a genetic programming approach, or another suitable technique) until the water treatment plan generator 12 provides the known outputs for all known input combinations stored in the databases 40.

In some embodiments, the water treatment model of the water treatment plan generator 12 may output a confidence score. The confidence score may provide an indication of how similar a given set of inputs are to information used to configure the ANN during training (e.g., the information stored on databases 40). In some embodiments, the confidence score may provide an indication as to whether additional training of the water treatment model is called for, and thus whether additional treatments, tests (e.g., bottle tests, field tests) may be necessary for generating additional water analysis information and treatment information for refining the water treatment model as described above.

Figure 3:
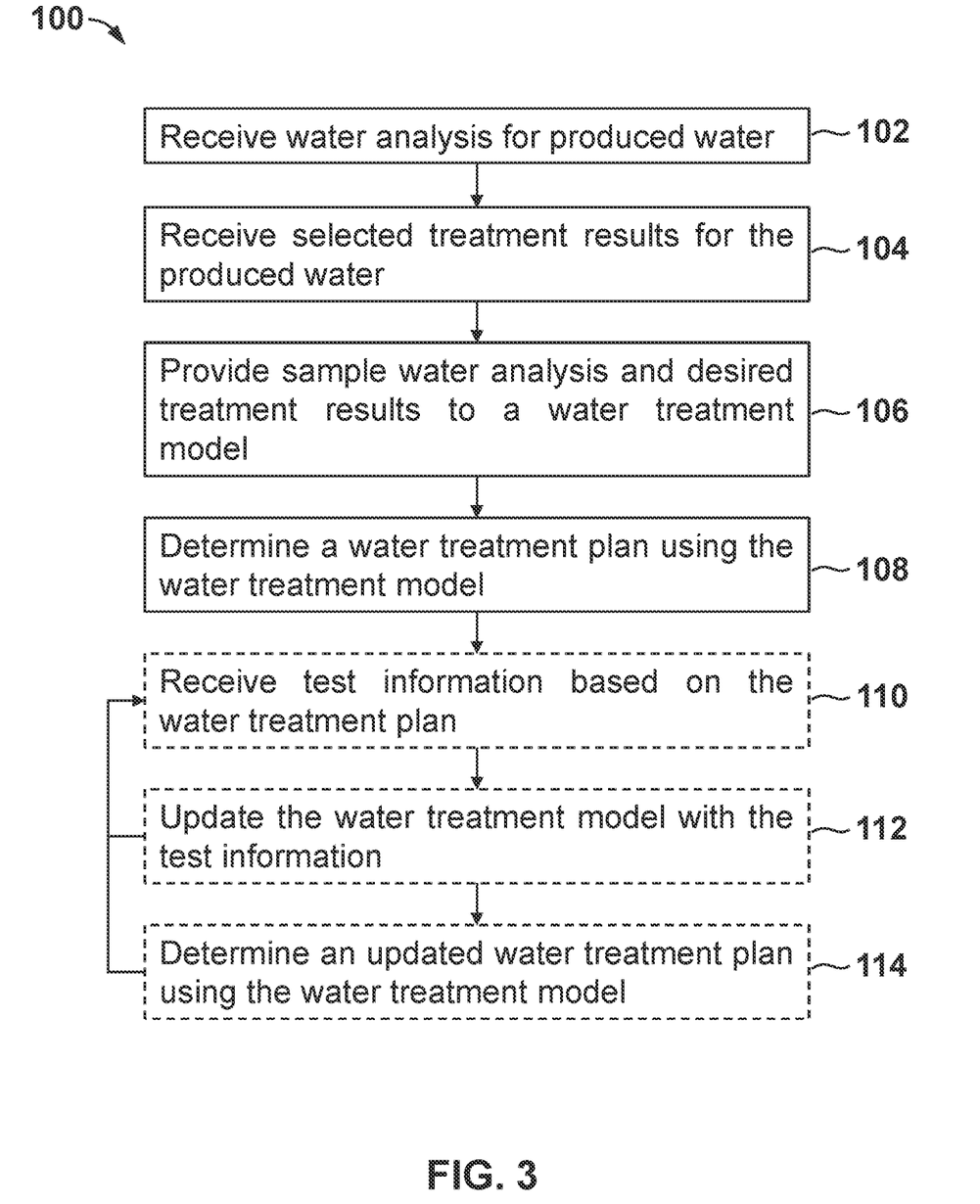
FIG. 3 is a flow diagram of a method of determining a water treatment plan according to some embodiments.

Referring to FIG. 3, a method 100 of determining a water treatment plan for produced water according to some embodiments is shown. In some embodiments, method 100 may be performed using the system 10, and thus, in describing the features of method 100, continuing reference may be made to FIG. 2. In addition, in some embodiments, some or all of the features of method 100 may be performed (at least partially) by a processor (e.g., processor 14) executing machine-readable instructions (e.g., machine-readable instructions 30). Thus, the method 100 may comprise a representation of the machine-readable instructions 30 according to some embodiments.

Method 100 includes receiving water analysis for a produced water sample at block 102. The water analysis may comprise any of the information included within the historical water analysis information previously described above. In some embodiments, the water analysis may be received by a processor (e.g., processor 14) via one or more suitable input devices (e.g., input device 18).

In addition, method 100 includes receiving selected treatment results for the produced water at block 104. The selected treatment results may comprise a desired characteristic, component, etc. of the produced water following treatment thereof. In some embodiments, the selected treatment results may comprise KPIs that are derived based on the water analysis received at block 102, and/or the characteristics or parameters of the wellbore to receive the injected produced water as generally described above. As with the water analysis, the selected treatment results may be received by a processor (e.g., processor 14) via one or more suitable input devices (e.g., input device 18).

Further, method 100 includes providing the water analysis and the selected treatment results to a water treatment model at block 106, and determining a water treatment plan with the water treatment model at block 108. The water treatment model may comprise a machine learning model (e.g., such as the machine learning model utilized by the water treatment plant generator 12 described above). Thus, the water treatment model may have been previously trained using labeled data that is stored in one or more databases (e.g., historical water analysis information and historical water treatment information stored on databases 40).

In some embodiments, the water treatment plan determined using the water treatment model at block 108 may be considered a final treatment plan that is then implemented on the produced water to improve one or more characteristics thereof for injection into a subterranean wellbore (e.g., wellbore 4 in FIG. 1). In some embodiments, determining a water treatment plan at block 108 may also comprise determining a confidence score for the water treatment plan as previously described above. If the confidence is score is high (e.g., above a threshold), this may serve as an indication that the water treatment plan will reliably produce the selected treatment results received at block 104 for the produced water.

On the other hand, if the confidence score is low (e.g., below a threshold), this may serve as an indication that the water treatment plan determined at block 108 may not reliably produce the selected treatment results received at block 104 (e.g., because the sample water analysis and/or the desired treatment results do not closely match the labeled data used to train the water treatment model). Thus, in the event of a low confidence score (or some other suitable indicator or decision), method 100 may include additional features for further refining the initial water treatment plan determined at block 108.

For instance, method 100 may include receiving test information based on the initial treatment plan at block 110. In some embodiments, the test information may be received at block 110 with a processor (e.g., processor 14) via one or more suitable input devices (e.g., input device 18).

The test information may comprise information similar to the historical water treatment information previously described, but that which corresponds to the produced water following treatment thereof based on the water treatment plan determined at block 108. The test information may be based on treatments and tests performed on one or more samples of the produced water (e.g., such as via one or more bottle tests) and/or may be based on treatments performed on larger volumes of water (e.g., such as via one or more field tests). The choice for conducting tests on small samples (e.g., via bottle tests) versus the larger, and thus more expensive, samples or volumes (e.g., via field test) of the produced water may be dictated by the confidence score (or other indicator(s)) generated with the water treatment plan via the water treatment model at block 108. For instance, if the confidence score is high (e.g., above a threshold), one may be more likely to conduct a larger scale field test to further refine or validate the water treatment plan determined at block 108. However, if the confidence score is low, then one may be more likely to conduct a series of smaller scale bottle tests to refine the water treatment plan.

Regardless of the type of test utilized to generate the test information, once the test information is received at block 110, method 100 includes updating the water treatment model with the test information at block 112. The water treatment model may be updated at block 110 by providing the test information and water analysis to the water treatment model as additional labeled data that may be used to further train and refine the model as generally described above (e.g., by adjusting one or more coefficients, parameters, etc. of the water treatment model). In some embodiments, the test information and water analysis may be provided to databases 40 as additional historical water analysis data and historical treatment data as previously described above.

In some embodiments, blocks 110, 112 may be repeated one or more times to provide additional test information that may be used to further refine the water treatment model. In some embodiments, the blocks 110, 112 may be repeated as a result of multiple treatments performed on the produced water (or samples thereof) to achieve one or more of the desired treatment results (e.g., KPIs). Repeated performance of blocks 110, 112 may also include receiving new or updated sample water analysis following a treatment of the produced water (or sample thereof) that may then be used to correspond to test information resulting from subsequent treatments of the same produced water (or samples thereof). The additional sample water analysis may be provided to the water treatment model along with the corresponding treatment information so as to further refine the model a block 112.

Further, at block 114, method 100 includes determining an updated water treatment plan with the water treatment model at block 114. The updated water treatment plan may be determined by providing the sample water analysis and desired treatment results from blocks 102 and 104, respectively, to the water treatment model that was updated via the test information via blocks 110 and 112 as previously described. Thus, the updated water treatment plan may be refined based on the adjusted parameters, coefficients, etc. within the water treatment model, and therefore may include a higher confidence score or other indicator.

In some embodiments, blocks 110, 112, 114 may be repeated until two successively determined water treatment plans (e.g., via block 108 and/or block 114) are the same or are substantially the same. This may result in a final water treatment plan that is associated with a high level of confidence (e.g., via a high confidence score) for producing the selected KPIs in the produced water.

Figure 4:
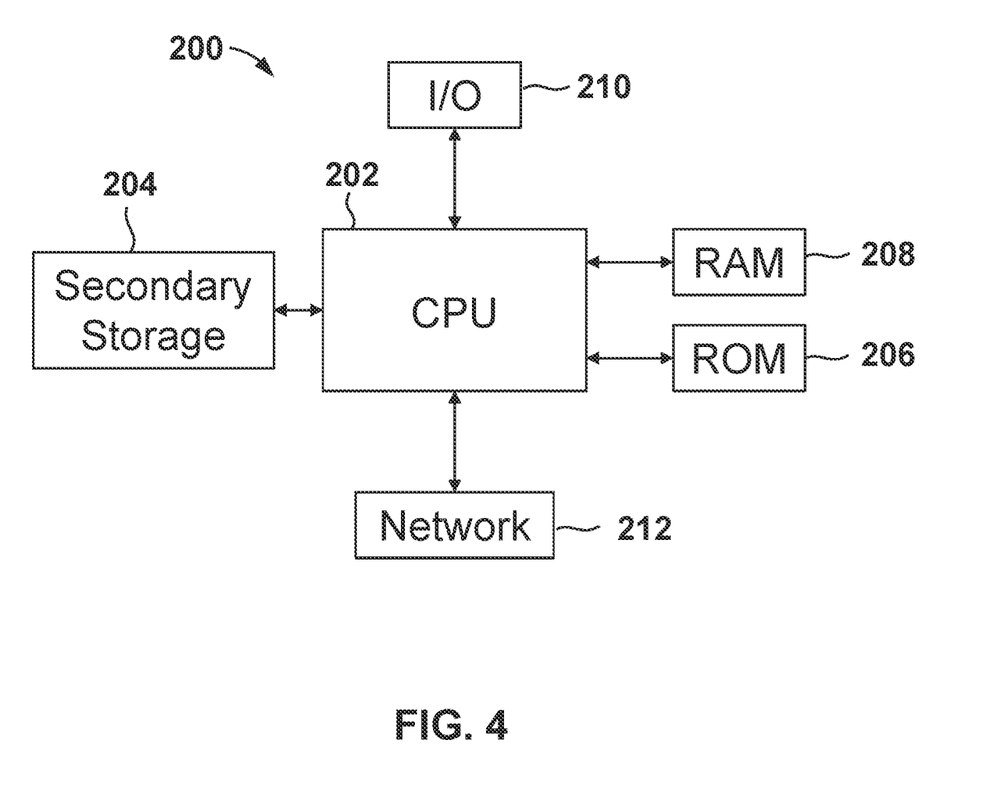
FIG. 4 is a schematic diagram of a computer system that may be utilized to implement the systems and method disclosed herein according to some embodiments.

FIG. 4 illustrates a computer system 200 suitable for implementing one or more embodiments disclosed herein. In particular, the computer system 200 may be implemented as the water treatment plan generator 12 (FIG. 2) in some embodiments. Thus, the following description of computer system 200 may be used to further illustrate particular features of embodiments of the water treatment plan generator 12 generally described above.

The computer system 200 includes a processor 202 (which may be referred to as a CPU) that is in communication with memory devices including secondary storage 204, ROM 206, RAM 208, input/output (I/O) devices 210, and network connectivity devices 212. The processor 202 may be implemented as one or more CPU chips.

It is understood that by programming and/or loading executable instructions onto the computer system 200, at least one of the CPU 202, the RAM 208, and the ROM 206 are changed, transforming the computer system 200 in part into a particular machine or apparatus having the novel functionality described herein. It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well-known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

Additionally, after the computer system 200 is turned on or booted, the CPU 202 may execute a computer program or application. For example, the CPU 202 may execute software or firmware stored in the ROM 206 or stored in the RAM 208 (e.g., machine readable instructions 30 shown in FIG. 2). In some cases, on boot and/or when the application is initiated, the CPU 202 may copy the application or portions of the application from the secondary storage 204 to the RAM 208 or to memory space within the CPU 202 itself, and the CPU 202 may then execute instructions that the application is comprised of. In some cases, the CPU 202 may copy the application or portions of the application from memory accessed via the network connectivity devices 212 or via the I/O devices 210 to the RAM 208 or to memory space within the CPU 202, and the CPU 202 may then execute instructions that the application is comprised of. During execution, an application may load instructions into the CPU 202, for example load some of the instructions of the application into a cache of the CPU 202. In some contexts, an application that is executed may be said to configure the CPU 202 to do something, e.g., to configure the CPU 202 to perform the function or functions promoted by the subject application. When the CPU 202 is configured in this way by the application, the CPU 202 becomes a specific purpose computer or a specific purpose machine.

The secondary storage 204 is typically comprised of one or more disk drives or tape drives and is used for non-volatile storage of data and as an over-flow data storage device if RAM 208 is not large enough to hold all working data. Secondary storage 204 may be used to store programs which are loaded into RAM 208 when such programs are selected for execution. The ROM 206 is used to store instructions and perhaps data which are read during program execution. ROM 206 is a non-volatile memory device which typically has a small memory capacity relative to the larger memory capacity of secondary storage 204. The RAM 208 is used to store volatile data and perhaps to store instructions. Access to both ROM 206 and RAM 208 is typically faster than to secondary storage 204. The secondary storage 204, the RAM 208, and/or the ROM 206 may be referred to in some contexts as computer readable storage media and/or non-transitory computer readable media.

I/O devices 210 (e.g., input device 18, output device 20 shown in FIG. 2) may include printers, video monitors, liquid crystal displays (LCDs), touch screen displays, keyboards, keypads, switches, dials, mice, track balls, voice recognizers, card readers, paper tape readers, or other well-known input devices.

The network connectivity devices 212 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards, and/or other well-known network devices. The network connectivity devices 212 may provide wired communication links and/or wireless communication links (e.g., a first network connectivity device 212 may provide a wired communication link and a second network connectivity device 212 may provide a wireless communication link). Wired communication links may be provided in accordance with Ethernet (IEEE 802.3), Internet protocol (IP), time division multiplex (TDM), data over cable service interface specification (DOCSIS), wavelength division multiplexing (WDM), and/or the like. In an embodiment, the radio transceiver cards may provide wireless communication links using protocols such as code division multiple access (CDMA), global system for mobile communications (GSM), long-term evolution (LTE), WiFi (IEEE 802.11), BLUETOOTH®, Zigbee, narrowband Internet of things (NB IoT), near field communications (NFC), radio frequency identity (RFID). The radio transceiver cards may promote radio communications using 5G, 5G New Radio, or 5G LTE radio communication protocols. These network connectivity devices 212 may enable the processor 202 to communicate with the Internet or one or more intranets. With such a network connection, it is contemplated that the processor 202 might receive information from the network, or might output information to the network in the course of performing the above-described method steps. Such information, which is often represented as a sequence of instructions to be executed using processor 202, may be received from and outputted to the network, for example, in the form of a computer data signal embodied in a carrier wave.

Such information, which may include data or instructions to be executed using processor 202 for example, may be received from and outputted to the network, for example, in the form of a computer data baseband signal or signal embodied in a carrier wave. The baseband signal or signal embedded in the carrier wave, or other types of signals currently used or hereafter developed, may be generated according to several methods well-known to one skilled in the art. The baseband signal and/or signal embedded in the carrier wave may be referred to in some contexts as a transitory signal.

The processor 202 executes instructions, codes, computer programs, scripts which it accesses from hard disk, floppy disk, optical disk (these various disk based systems may all be considered secondary storage 204), flash drive, ROM 206, RAM 208, or the network connectivity devices 212. While only one processor 202 is shown, multiple processors may be present. Thus, while instructions may be discussed as executed by a processor, the instructions may be executed simultaneously, serially, or otherwise executed by one or multiple processors. Instructions, codes, computer programs, scripts, and/or data that may be accessed from the secondary storage 204, for example, hard drives, floppy disks, optical disks, and/or other device, the ROM 206, and/or the RAM 208 may be referred to in some contexts as non-transitory instructions and/or non-transitory information.

In an embodiment, the computer system 200 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computer system 200 to provide the functionality of a number of servers that is not directly bound to the number of computers in the computer system 200. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In an embodiment, some or all of the functionality disclosed above may be provided as a computer program product. The computer program product may comprise one or more machine-readable storage medium having computer usable program code embodied therein to implement the functionality disclosed above. The computer program product may comprise data structures, executable instructions, and other computer usable program code. The computer program product may be embodied in removable machine storage media and/or non-removable machine storage media. The removable machine-readable storage medium may comprise, without limitation, a paper tape, a magnetic tape, magnetic disk, an optical disk, a solid state memory chip, for example analog magnetic tape, compact disk read only memory (CD-ROM) disks, floppy disks, jump drives, digital cards, multimedia cards, and others. The computer program product may be suitable for loading, by the computer system 200, at least portions of the contents of the computer program product to the secondary storage 204, to the ROM 206, to the RAM 208, and/or to other non-volatile memory and volatile memory of the computer system 200. The processor 202 may process the executable instructions and/or data structures in part by directly accessing the computer program product, for example by reading from a CD-ROM disk inserted into a disk drive peripheral of the computer system 200. Alternatively, the processor 202 may process the executable instructions and/or data structures by remotely accessing the computer program product, for example by downloading the executable instructions and/or data structures from a remote server through the network connectivity devices 212. The computer program product may comprise instructions that promote the loading and/or copying of data, data structures, files, and/or executable instructions to the secondary storage 204, to the ROM 206, to the RAM 208, and/or to other non-volatile memory and volatile memory of the computer system 200.

In some contexts, the secondary storage 204, the ROM 206, and the RAM 208 may be referred to as a non-transitory computer readable medium or a computer readable storage media. A dynamic RAM embodiment of the RAM 208, likewise, may be referred to as a non-transitory machine-readable medium in that while the dynamic RAM receives electrical power and is operated in accordance with its design, for example during a period of time during which the computer system 200 is turned on and operational, the dynamic RAM stores information that is written to it. Similarly, the processor 202 may comprise an internal RAM, an internal ROM, a cache memory, and/or other internal non-transitory storage blocks, sections, or components that may be referred to in some contexts as non-transitory machine-readable media or machine-readable storage media.

The embodiments disclosed herein include systems and methods for determining a treatment plan for produced water. In some embodiments, the systems may comprise a water treatment plan generator (e.g., water treatment plan generator 12) that provides various inputs (e.g., parameters of the produced water, wellbore, subterranean formation) to a machine-learning model (e.g., a water treatment model) that outputs a water treatment plan. Thus, through use of the embodiments disclosed herein, a well operator may more quickly and efficiently arrive at a suitable water treatment plan for produced water, so as to reduce costs associated with water injection operations.

While exemplary embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the disclosure. Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simplify subsequent reference to such steps.

What is claimed is:

1. A method for determining a water treatment plan for produced water originating from a subterranean formation, the method comprising:
   receiving sample water analysis for the produced water;
   receiving one or more key performance indicators (KPIs) that each indicate a selected treatment result for the produced water;
   providing the sample water analysis and the KPIs to a machine learning model;
   determining a water treatment plan for the produced water using the machine learning model, wherein the water treatment plan comprises one or more additives for the produced water that are to provide the produced water with the KPIs;
   testing the water treatment plan on a sample of the produced water;
   analyzing the sample of the produced water after the testing to produce test information;
   updating the machine learning model with the test information to produce an updated machine learning model;
   providing the sample water analysis and the KPIs to the updated machine learning model; and
   determining an updated water treatment plan for the produced water with the updated machine learning model; and determining a confidence score for the water treatment model based on a difference between the sample water analysis and historical water analysis information, wherein the historical water analysis information comprises primary component analysis (PCA) for a plurality of water samples, wherein testing the water treatment plan on a sample of the produced water comprises performing a bottle test or a field test based on the confidence score.

2. The method of claim 1, wherein the water treatment plan comprises relative amounts of the one or more additives for the produced water, and wherein the machine learning model comprises an artificial neural network.

3. The method of claim 1, comprising:
training the machine learning model with the historical water analysis information and historical water treatment information stored in one or more databases;
wherein the historical water treatment information comprises water treatment plans and KPIs for the plurality of water samples; and
wherein the historical water analysis information and the historical water treatment information are related to one another in the one or more databases.

4. The method of claim 3, comprising:
storing the sample water analysis for the produced water in the one or more databases as historical water analysis information; and
storing the water treatment plan, and the KPIs in the one or more databases as historical water treatment information.

5. The method of claim 3, comprising:
determining that the confidence score is below a threshold; and
updating the machine learning model based on the determination that the confidence score is below the threshold.

6. The method of claim 1, wherein the one or more additives comprises one or more oxidizers, biocides, reducing agents, scale inhibitors, corrosion inhibitors, chelating agents, coagulants, viscosifiers, rheology modifiers, dispersants, flocculants, floatation aids, surfactants, emulsifiers, demulsifiers, foamers, and defoamers.

7. The method of claim 1, wherein the one or more additives comprises a biochelant that is produced using a biological catalyst.

8. A system for determining a water treatment plan for produced water originating from a subterranean formation, the system comprising:
one or more samples of the produced water;
an input device;
an output device; and
a water treatment plan generator coupled to the input device and the output device, wherein the water treatment plan generator is configured to:
receive water sample analysis associated with a first sample off the produced water via the input device;
receive one or more key performance indicators (KPIs) for the produced water via the input device, wherein each of the KPIs indicate a selected treatment result for the produced water;
provide the sample water analysis and the KPIs to a machine learning model;
determine a water treatment plan for the produced water using the machine learning model, wherein the water treatment plan comprises one or more additives for the produced water that are to provide the produced water with the KPIs;
receive test information, via the input device based upon testing the water treatment plan on a second sample of the produced water;
analyze the test information;
update the machine learning model with the test information to produce an updated machine learning model;
provide the sample water analysis and the KPIs to the updated machine learning model;
determine an updated water treatment plan for the produced water with the updated machine learning model; and
determine a confidence score for the water treatment plan based on a difference between the sample water analysis and historical water analysis information, wherein the historical water analysis information comprises primary component analysis (PCA) for a plurality of water samples, and wherein the test information is obtained by performing a bottle fest or a field test based on the confidence score; and
communicate the water treatment plan to the output device.

9. The system of claim 8, wherein the water treatment plan comprises relative amounts of the one or more additives for the produced water, and wherein the machine learning model comprises an artificial neural network.

10. The system of claim 8, wherein water treatment plan generator is configured to:
receive test information for the produced water via the input device, wherein the test information comprises an analysis of a sample of the produced water after treatment using the water treatment plan determined by the water treatment plan generator;
update the machine learning model with the test information to produce an updated machine learning model;
provide the sample water analysis and the KPIs to the updated machine learning model; and
determine an updated water treatment plan for the produced water with the updated machine learning model.

11. The system of claim 8, wherein the water treatment plan generator comprises one or more databases that store:
the historical water analysis information comprising the PCA plurality of water samples; and
historical water treatment information comprising water treatment plans and KPIs for the plurality of water samples;
wherein the historical water analysis information and the historical water treatment information are related to one another in the one or more databases.

12. The system of claim 11, wherein the water treatment plan generator is configured to:
determine a confidence score for the water treatment model based on a difference between the sample water analysis and the historical water analysis information;
determine that the confidence score is below a threshold; and
update the machine learning model based on the determination that the confidence score is below the threshold.

13. The system of claim 8, wherein the one or more additives comprises one or more oxidizers, biocides, reducing agents, scale inhibitors, corrosion inhibitors, chelating agents, coagulants, viscosifiers, rheology modifiers, dispersants, flocculants, floatation aids, surfactants, emulsifiers, demulsifiers, foamers, and defoamers.

14. The system of claim 8, wherein the one or more additives comprises a biochelant that is produced using a biological catalyst.

15. The system of claim 8, wherein the water treatment plan generator is configured to:

select either the bottle test or the field test to produce the test information based on the confidence score.

16. A system for determining a water treatment plan for produced water originating from a subterranean formation, the system comprising:

one or more samples of the produced water; and a non-transitory, machine-readable medium comprising instructions, that when executed by a processor, cause the processor to:

receive sample water analysis for produced water that originated from a subterranean formation;

receive one or more key performance indicators (KPIs) that each indicate a selected treatment result for the produced water;

provide the sample water analysis and the KPIs to a machine learning model;

determine a water treatment plan for the produced water using the machine learning model, wherein the water treatment plan comprises one or more additives for the produced water that are to provide the produced water with the KPIs;

receive test information for the produced water, wherein the test information comprises an analysis of sample of the produced water after treatment using the water treatment plan;

update the machine learning model with the test information to produce an updated machine learning model;

provide the sample water analysis and the KPIs to the updated machine learning model;

determine an updated water treatment plan for the produced water with the updated machine learning model; and determine a confidence score for the water treatment plan based on a difference between the sample water analysis and historical water analysis information, wherein the historical water analysis information comprises primary component analysis (PCA) for a plurality of water samples.

17. The system of claim 16, wherein the one or more additives comprises one or more oxidizers, biocides, reducing agents, scale inhibitors, corrosion inhibitors, chelating agents, coagulants, viscosifiers, rheology modifiers, dispersants, flocculants, floatation aids, surfactants, emulsifiers, demulsifiers, foamers, and defoamers.

18. The system of claim 17, wherein the one or more additives comprises a biochelant that is produced using a biological catalyst.

* * * * *